United States Patent
Patel et al.

(10) Patent No.: US 9,326,945 B2
(45) Date of Patent: May 3, 2016

(54) APIXABAN FORMULATIONS

(75) Inventors: Jatin Patel, West Windsor, NJ (US);
Charles Frost, Yardley, PA (US);
Jingpin Jia, Belle Mead, NJ (US);
Chandra Vemavarapu, Hillsborough, NJ (US)

(73) Assignees: Bristol-Myers Squibb Company, Princeton, NJ (US); Pfizer Inc., New York, NY (US)

( * ) Notice: Subject to any disclaimer, the term of this patent is extended or adjusted under 35 U.S.C. 154(b) by 0 days.

(21) Appl. No.: 13/579,796

(22) PCT Filed: Feb. 24, 2011

(86) PCT No.: PCT/US2011/025994
§ 371 (c)(1),
(2), (4) Date: Oct. 10, 2012

(87) PCT Pub. No.: WO2011/106478
PCT Pub. Date: Sep. 1, 2011

(65) Prior Publication Data
US 2013/0045245 A1    Feb. 21, 2013

Related U.S. Application Data

(60) Provisional application No. 61/308,056, filed on Feb. 25, 2010.

(51) Int. Cl.
*A61K 9/20* (2006.01)
*A61K 31/4545* (2006.01)
*A61K 31/437* (2006.01)
*A61K 31/4412* (2006.01)

(52) U.S. Cl.
CPC ............ *A61K 9/2018* (2013.01); *A61K 9/2013* (2013.01); *A61K 9/2054* (2013.01); *A61K 9/2095* (2013.01); *A61K 31/4545* (2013.01); *A61K 31/437* (2013.01); *A61K 31/4412* (2013.01)

(58) Field of Classification Search
None
See application file for complete search history.

(56) References Cited

U.S. PATENT DOCUMENTS

| | | | |
|---|---|---|---|
| 6,150,366 A | 11/2000 | Arenson et al. | |
| 6,967,208 B2 | 11/2005 | Pinto et al. | |
| 7,396,932 B2 | 7/2008 | Shapiro et al. | |
| 2006/0069258 A1 | 3/2006 | Shapiro et al. | |

(Continued)

FOREIGN PATENT DOCUMENTS

| CN | 1578660 A | 2/2005 |
|---|---|---|
| CN | 101516355 A | 8/2009 |

(Continued)

OTHER PUBLICATIONS

Official Action in Mexican Application No. MX/2012/060772 (issued Jun. 14, 2013).

(Continued)

*Primary Examiner* — Bethany Barham
*Assistant Examiner* — Barbara Frazier
(74) *Attorney, Agent, or Firm* — Fitzpatrick, Cella, Harper & Scinto

(57) ABSTRACT

Compositions comprising crystalline apixaban particles having a $D_{90}$ equal to or less than 89 μm, and a pharmaceutically acceptable carrier, are substantially bioequivalent and can be used to for the treatment and/or prophylaxis of thromboembolic disorders.

38 Claims, 4 Drawing Sheets

Dissolution Rates of 2.5-mg Apixaban Tablets Using Drug Substance of Different Particle Size

(56) References Cited

U.S. PATENT DOCUMENTS

| | | | |
|---|---|---|---|
| 2006/0160841 A1 | 7/2006 | Wei et al. | |
| 2008/0279845 A1* | 11/2008 | Conley et al. | 424/130.1 |
| 2009/0123390 A1* | 5/2009 | Hill | 424/45 |
| 2009/0285887 A1* | 11/2009 | Abu-Baker et al. | 424/469 |
| 2012/0087978 A1 | 4/2012 | Nause | |
| 2013/0072512 A1* | 3/2013 | Jahagirdar et al. | 514/279 |

FOREIGN PATENT DOCUMENTS

| | | | |
|---|---|---|---|
| JP | 2005-507889 A | 3/2005 | |
| JP | 2008-514712 A | 5/2008 | |
| JP | 2008-537750 A | 9/2008 | |
| JP | 2010-502762 A | 1/2010 | |
| WO | 00/39131 A1 | 7/2000 | |
| WO | 2006/108643 A2 | 10/2006 | |
| WO | 2007/022165 A2 | 2/2007 | |
| WO | 2008/031782 A1 | 3/2008 | |
| WO | 2009/135947 A2 | 11/2009 | |
| WO | 2010/003811 A1 | 1/2010 | |
| WO | 2010/147978 A1 | 12/2010 | |

OTHER PUBLICATIONS

First Office Action in Chinese Application No. 201180011229.X (issued Aug. 9, 2013).
First Examination Report in New Zealand Application No. 601738 (Apr. 29, 2013).
Office Action in Colombian Application No. 12.152.138 (issued Nov. 5, 2013).
Communication pursuant to Article 94(3) EPC in European Application No. 11707284.3 (issued Jun. 28, 2013).
Amidon et al., "A Theoretical Basis for a Biopharmaceutic Drug Classification: The Correlation of in Vitro Product Dissolution and in Vivo Bioavailability", Pharmaceutical Research, vol. 12, pp. 413-420, 1995.
Office Action in Mexican Application No. MX/a/2012/009244 (issued Jun. 6, 2014).
J. Thompson, Práctica Contemporánea En Farmacia (2nd edition), p. 287 (2006).
Alfonso R. Gennaro, Remington, Farmacia. Medica Panamericana (20th edition), Chapter I, p. 1005 (2000).
Summons to attend oral proceedings pursuant to Rule 115(1) EPC in European Application No. 11707284.3 (dated Nov. 14, 2014).
Official Action in Mexican Application No. MX/a/2012/009244 (dated Feb. 10, 2015).
Notification of Reasons for Refusal in Japanese Patent Application No. 2012-555127 (notified Feb. 24, 2015).
Hiroshi Nakagawa et al., "Formulation of Insoluble Drug," 24(11) JJSHP 15-22 (1988).
Hideo Yamada, Pharmaceutics I: Drug Compounding/Formulation, Chapter 2: Pharmaceutical Preparation Method, pp. 62-76 (Asakura Publishing Co., Ltd., 1995).
Heiichirou Toubata, Granulation Handbook, Application of Pelletization, pp. 438-439 (Japan Powder Industry Association, 1975).
Akinobu Ohtsuka et al., Pharmaceutics, Chapter 4 : Unit Operation of Powder Preparation, pp. 104-105 (Hirokawa Publishing Co., Ltd., 1976).

Office Action in Russian Application No. 2012140690 (dated Feb. 12, 2015).
Dressman et al., "The BCS: Where Do We Go from Here?" Pharmaceutical Technology, pp. 68-76 (Jul. 2001).
Third Party Observations in European Application No. 11707284.3 (dated May 19, 2015).
Notification Concerning the Date of Oral Proceedings in European Application No. 11707284.3 (dated May 12, 2015).
Notification Concerning the Date of Oral Proceedings in European Application No. 11707284.3 (dated May 27, 2015).
Official Action in Israeli Application No. 221064 (dated May 10, 2015).
Technical Report No. EDM 36/2015 in Peruvian Application No. 001362-2012 (dated Jul. 9, 2015).
Opposition to Peruvian Application No. 001362-2012 (dated Jun. 20, 2013).
Third Party Observations in European Application No. 11707284.3 (dated Jul. 30, 2014).
Third Party Observations in European Application No. 11707284.3 (dated Jul. 15, 2014).
Third Party Observations in European Application No. 11707284.3 (dated Aug. 18, 2014).
European Pharmacopoeia 6.0; Section 2.9.31—"Particle Size Analysis by Laser Light Diffraction", pp. 311-314 (Jul. 2007).
European Pharmacopoeia 7.0; Section 2.9.31—"Particle Size Analysis by Laser Light Diffraction", pp. 295-299 (Jul. 2010).
Resolution N° 61405 in Colombian Application No. 12.152.138 (dated Oct. 14, 2014).
Peng Chen et al., "Enhancement for Dissolution of Poorly Water Soluble Drug by Micronization," 10 Chemistry Bulletin 766-771 (2007).
Second Office Action in Chinese Application No. 201180011229.X (issued Oct. 31, 2014).
Third Party Observations in European Application No. 11707284.3 (filed Jan. 16, 2015).
International Standard—ISO 13320-1, First Edition, Particle Size Analysis—Laser Diffraction Methods, pp. 1-34 (Nov. 1999).
Nor Hafizah Hj Annuar et al., "Effects of Sample Conditions on Multi-Particle Size Analysis Using Laser Diffraction Technique," Scientia Bruneiana, pp. 19-26 (2010).
Zoran Stojanovic et al., "Determination of Particle Size Distributions by Laser Diffraction," 21 Technics—New Materials 11-20 (2012).
Third Party Observations on European Application No. 11707284.3 (dated Jul. 24, 2015).
U.S. Pharmacopoeia (USP) 38, Chapter 429, "Light Diffraction Measurement of Particle Size," pp. 294-299 (May 2015) (Annex 1).
Third Office Action in Chinese Application No. 201180011229X (notified Dec. 11, 2015).
Resolution No. 39058 in Colombian Application No. 12.152.138 (published Aug. 4, 2015).
Resolution No. 64634 in Colombian Application No. 14.268.266 (published Sep. 22, 2015).
Office Action in Russian Application No. 2012140690 (dated Dec. 18, 2015).
Extended European Search Report in European Application No. 15190823.3 (Feb. 3, 2016).
Technical Report No. EDM 008-2016/A in Peruvian Application No. 001362-2012 (Mar. 7, 2016).

* cited by examiner

Figure 1: Scatter Plot of Individual Dose-Normalized AUC(INF) Values for Solutions (CV185001, CV185006, and CV185007) and Tablets (CV185001 and CV185024)

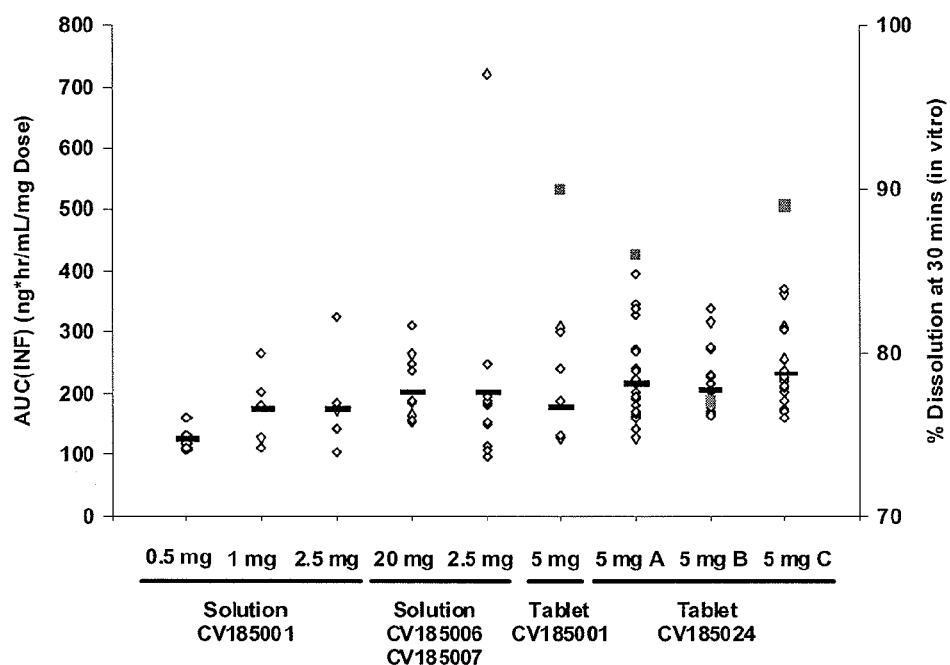

*Source*: CV185001, CV185006, CV185007, and CV185024 Clinical Study Reports

The solid line represents the geometric mean of AUC(INF) and the solid square represents the average %in-vitro dissolved at 30 minutes (using QC method in Table 1.2C). The X-axis represents the dose administered.

For CV185024, 5 mg A = Apixaban Phase 2 tablet (86% dissolution) 2x2.5 mg (reference formulation), 5 mg B = Apixaban Phase 2 tablet (77% dissolution) 2x2.5 mg, 5 mg C = Apixaban Phase 3 tablet (89% dissolution) 2x2.5 mg.

Figure 2: Scatter Plot of Individual Dose Normalized Cmax Values for Solutions (CV185001, CV185006, and CV185007) and Tablets (CV185001 and CV185024)

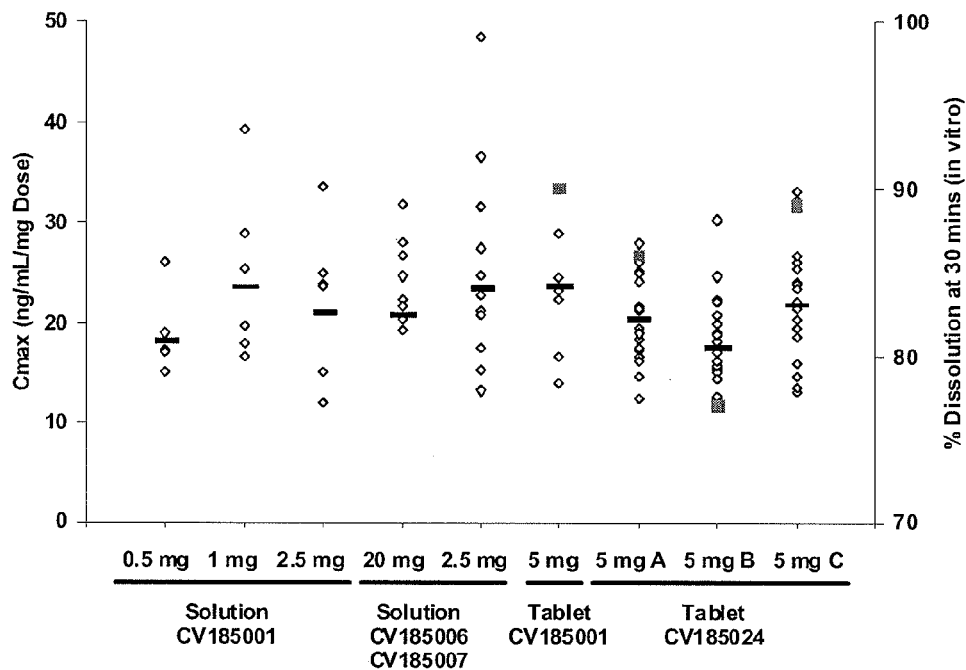

*Source*: CV185001, CV185006, CV185007, and CV185024 Clinical Study Reports

The solid line represents the geometric mean of Cmax and the solid square represents the average %in-vitro dissolved at 30 minutes (using QC method in Table 1.2C). The X-axis represents the dose administered.

For CV185024, 5 mg A = Apixaban Phase 2 tablet (86% dissolution) 2x2.5 mg (reference formulation), 5 mg B = Apixaban Phase 2 tablet (77% dissolution) 2x2.5 mg, 5 mg C = Apixaban Phase 3 tablet (89% dissolution) 2x2.5 mg.

Figure 3: Dissolution Rates of 2.5-mg Apixaban Tablets Using Drug Substance of Different Particle Size
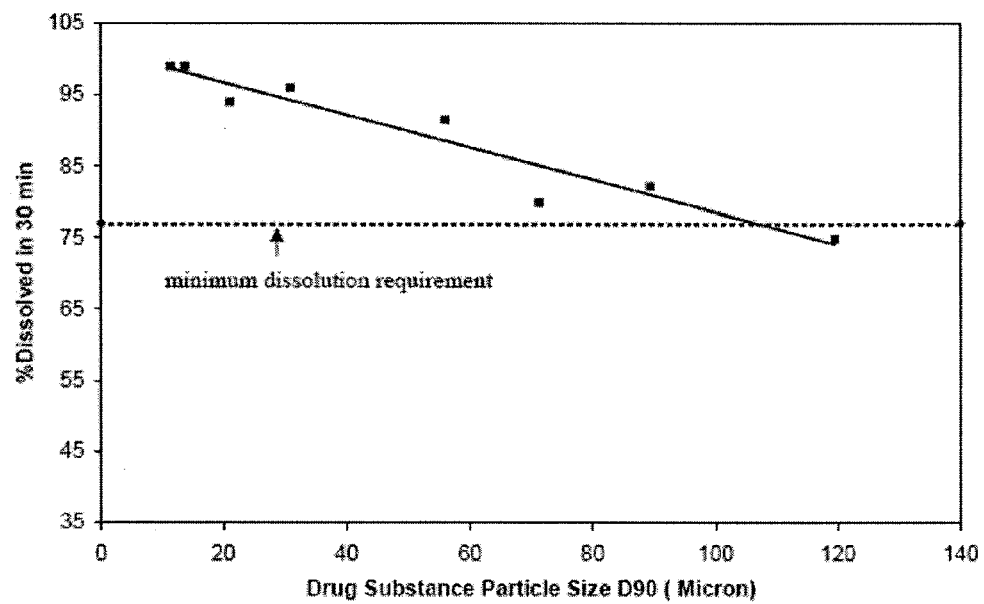

Figure 4: Dissolution Rates of 5-mg Apixaban Tablets Using Drug Substance of Different Particle Size
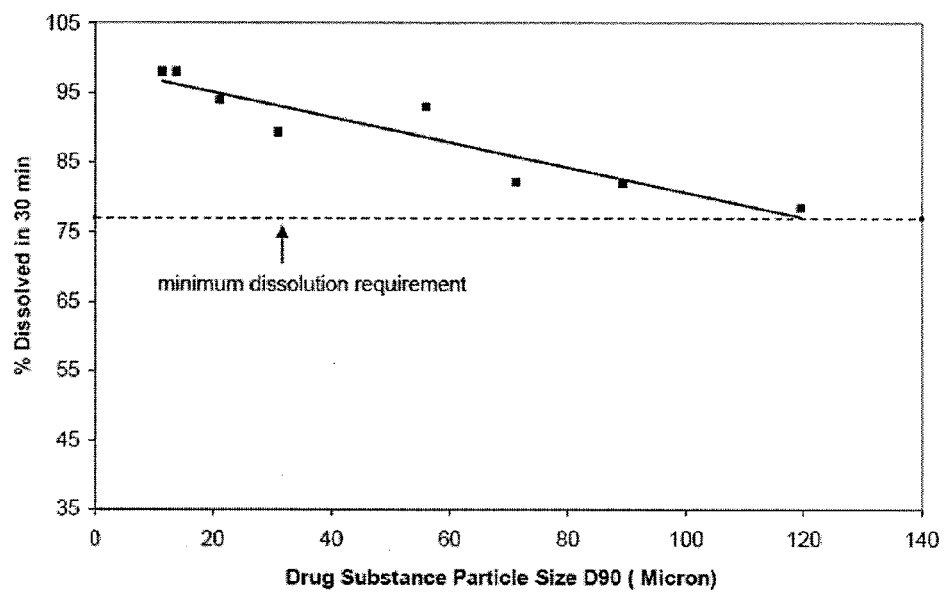

APIXABAN FORMULATIONS

This application is the National Stage of International Application No. PCT/US2011/025994, filed Feb. 24, 2011, which claims the benefit of U.S. Provisional Application No. 61/308,056, filed Feb. 25, 2010.

FIELD OF THE INVENTION

This invention relates to apixaban pharmaceutical formulations comprising crystalline apixaban particles having a maximum size cutoff; and methods of using them, for example, for the treatment and/or prophylaxis of thromboembolic disorders.

BACKGROUND OF THE INVENTION

Apixaban is a known compound having the structure:

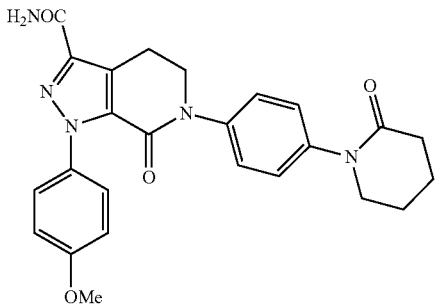 [SMILES: COc1ccc(-n2nc(C(N)=O)c3c2C(=O)N(c2ccc(N4CCCCC4=O)cc2)CC3)cc1]

The chemical name for apixaban is 4,5,6,7-tetrahydro-1-(4-methoxyphenyl)-7-oxo-6-[4-(2-oxo-1-piperidinyl)phenyl]-1H-pyrazolo[3,4-c]pyridine-3-carboxamide (CAS name) or 1-(4-methoxyphenyl)-7-oxo-6-[4-(2-oxo-1-piperidinyl)phenyl]-4,5,6,7-tetrahydro-1H-pyrazolo[3,4-c]pyridine-3-carboxamide (IUPAC name).

Apixaban is disclosed in U.S. Pat. No. 6,967,208 (based on U.S. application Ser. No. 10/245,122 filed Sep. 17, 2002), which is herein incorporated by reference in its entirety, has utility as a Factor Xa inhibitor, and is being developed for oral administration in a variety of indications that require the use of an antithrombotic agent.

The aqueous solubility (40 µg/mL at all physiological pH) of apixaban suggests that the tablets with less than 10 mg apixaban (dose/solubility ratio=250 mL) should not demonstrate dissolution rate limited absorption since dissolution rate limitations are only expected when the dose/solubility ratio is greater than 250 mL. Based on this dose and solubility consideration, the particle size of the compound should not be critical for achieving consistent plasma profiles, according to the prediction based on the Biopharmaceutics Classification System (BCS; Amidon, G. L. et al., *Pharmaceutical Research*, 12: 413-420 (1995)). However, it was determined that formulations that were made using a wet granulation process as well as those using large particles of apixaban drug substance resulted in less than optimal exposures, which can present quality control challenges.

SUMMARY OF THE INVENTION

Surprisingly and unexpectedly, it has been found that compositions for tablets comprising up to 5 mg, apixaban particles having a $D_{90}$ (90% of the volume) less than 89 microns (µm) lead to consistent in-vivo dissolution in humans (at physiologic pH), hence, consistent exposure and consistent Factor Xa inhibition that will lead to consistency in therapeutic effect. Consistent exposure is defined as that where in-vivo exposure from tablets is similar to that from a solution and not affected by the differences in dissolution rates. The compositions were prepared using a dry granulation process. Accordingly, the invention provides a pharmaceutical composition comprising crystalline apixaban particles having a $D_{90}$ equal to or less than about 89 µm as measured by laser light scattering method, and a pharmaceutically acceptable diluent or carrier. It is preferred that the apixaban particles in the composition have a $D_{90}$ not exceeding 89 µm. It is noted the notation $D_X$ means that X % of the volume of particles have a diameter less than a specified diameter D. Thus a $D_{90}$ of 89 µm means that 90% of the volume of particles in an apixaban composition have a diameter less than 89 µm.

The range of particle sizes preferred for use in the invention is $D_{90}$ less than 89 µm, more preferably $D_{90}$ less than 50 µm, even more preferably $D_{90}$ less than 30 µm, and most preferably $D_{90}$ less than 25 µm. The particle sizes stipulated herein and in the claims refer to particle sizes were determined using a laser light scattering technique.

The invention further provides the pharmaceutical composition further comprising a surfactant from 0.25% to 2% by weight, preferably from 1% to 2% by weight. As regards the surfactant, it is generally used to aid in wetting of a hydrophobic drug in a tablet formulation to ensure efficient dissolution of the drug, for example, sodium lauryl sulfate, sodium stearate, polysorbate 80 and poloxamers, preferably sodium lauryl sulfate.

The invention further provides a method for the treatment or prophylaxis of thromboembolic disorders, comprising administering to a patient in need of such treatment or prophylaxis a therapeutically effective amount of a composition comprising crystalline apixaban particles having a $D_{90}$ equal to or less than about 89 µm as measured by laser light scattering, and a pharmaceutically acceptable carrier.

The present invention also provides a dry granulation process for preparing a composition comprising crystalline apixaban particles having a $D_{90}$ equal to or less than about 89 µm as measured by laser light scattering, and a pharmaceutically acceptable carrier.

The formulations of this invention are advantageous because, inter alia, as noted above, they lead to consistent human in-vivo dissolution. The invention is surprising in this respect, however, in that exposures are variable even though apixaban has adequate aqueous solubility that would allow the drug to dissolve rapidly. That is, one would expect dissolution rate for a drug that has high solubility (as defined by the Biopharmaceutical Classification System) would not be limited by the particle size. It has surprisingly been found, however, that the particle size that impacts apixaban absorption rate is about a $D_{90}$ of 89 µm. Thus apixaban can be formulated in a composition having a reasonable particle size using dry granulation process, to achieve and maintain relatively fine particles to facilitate consistent in vivo dissolution.

In a relative bioavailabiltiy study where various apixaban formulations were evaluated, it was determined that formulations made using a wet granulation process resulted in lower exposures compared to the exposures obtained from a dry granulation process. Additionally, tablets made using larger particles ($D_{90}$ of 89 µm) had lower exposures compared to tablets made using the same process but with particle size of $D_{90}$ of 50 µm. In a dry granulation process, water is not used during manufacturing to develop granules containing apixaban and the excipients.

Formulations according to this invention, when dissolution tested in vitro preferably exhibit the following dissolution criteria. That is, the formulation exhibits dissolution properties such that, when an amount of the drug equivalent to 77% therein dissolves within 30 minutes. Usually the test result is established as an average for a pre-determined number of dosages (e.g., tablets, capsules, suspensions, or other dosage form), usually 6. The dissolution test is typically performed in an aqueous media buffered to a pH range (1 to 7.4) observed in the gastrointestinal tract and controlled at 37° C. (±1° C.), together maintaining a physiological relevance. It is noted that if the dosage form being tested is a tablet, typically paddles rotating at 50-75 rpm are used to test the dissolution rate of the tablets. The amount of dissolved apixaban can be determined conventionally by HPLC, as hereinafter described. The dissolution (in-vitro) test is developed to serve as a quality control tool, and more preferably to predict the biological (in-vivo) performance of the tablet, where invivo-invitro relationships (IVIVR) are established.

The term "particles" refers to individual drug substance particles whether the particles exist singly or are agglomerated. Thus, a composition comprising particulate apixaban may contain agglomerates that are well beyond the size limit of about 89 μm specified herein. However, if the mean size of the primary drug substance particles (i.e., apixaban) comprising the agglomerate are less than about 89 μm individually, then the agglomerate itself is considered to satisfy the particle size constraints defined herein and the composition is within the scope of the invention.

Reference to apixaban particles having "a mean particle size" (herein also used interchangeably with "VMD" for "volume mean diameter") equal to or less than a given diameter or being within a given particle size range means that the average of all apixaban particles in the sample have an estimated volume, based on an assumption of spherical shape, less than or equal to the volume calculated for a spherical particle with a diameter equal to the given diameter. Particle size distribution can be measured by laser light scattering technique as known to those skilled in the art and as further disclosed and discussed below.

"Bioequivalent" as employed herein means that if a dosage form is tested in a crossover study (usually comprising a cohort of at least 10 or more human subjects), the average Area under the Curve (AUC) and/or the $C_{max}$ for each crossover group is at least 80% of the (corresponding) mean AUC and/or $C_{max}$ observed when the same cohort of subjects is dosed with an equivalent formulation and that formulation differs only in that the apixaban has a preferred particle size with a $D_{90}$ in the range from 30 to 89 μm. The 30 μm particle size is, in effect, a standard against which other different formulations can be compared. AUCs are plots of serum concentration of apixaban along the ordinate (Y-axis) against time for the abscissa (X-axis). Generally, the values for AUC represent a number of values taken from all the subjects in a patient population and are, therefore, mean values averaged over the entire test population. C.sub.max, the observed maximum in a plot of serum level concentration of apixaban (Y-axis) versus time (X-axis) is likewise an average value.

Use of AUCs, $C_{max}$, and crossover studies is, of course otherwise well understood in the art. The invention can indeed be viewed in alternative terms as a composition comprising crystalline apixaban particles having a mean particle size equal to or less than about 89 μm, as measured by Malvern light scattering, and a pharmaceutically acceptable carrier, said composition exhibiting a mean AUC and/or mean $C_{max}$ which are at least 80% of the corresponding mean AUC and/or $C_{max}$ values exhibited by a composition equivalent thereto (i.e., in terms of excipients employed and the amount of apixaban) but having an apixaban mean particle size of 30 μm. Use of the term "AUC" for purposes of this invention implies crossover testing within a cohort of at least 10 healthy subjects for all compositions tested, including the "standard" 30 μm particle size composition.

The present invention may be embodied in other specific forms without departing from the spirit or essential attributes thereof. Thus, the above embodiments should not be considered limiting. Any and all embodiments of the present invention may be taken in conjunction with any other embodiment or embodiments to describe additional embodiments. Each individual element of the embodiments is its own independent embodiment. Furthermore, any element of an embodiment is meant to be combined with any and all other elements from any embodiment to describe an additional embodiment. In addition, the present invention encompasses combinations of different embodiment, parts of embodiments, definitions, descriptions, and examples of the invention noted herein.

BRIEF DESCRIPTION OF THE DRAWINGS

FIG. 1 is a scatter plot of individual dose-normalized AUC (INF) values for solutions (CV185001, CV185006, and CV185007) and tablets (CV185001 and CV185024).

FIG. 2 is scatter plot of individual dose-normalized $C_{max}$ values for solutions (CV185001, CV185006, and CV185007) and tablets (CV185001 and CV185024).

FIG. 3 is a plot of dissolution rates of 2.5 mg apixaban tablets using drug substance of different particle size.

FIG. 4 is a plot of dissolution rates of 5 mg apixaban tablets using drug substance of different particle size.

DETAILED DESCRIPTION OF THE INVENTION

As previously stated, apixaban in any form which will crystallize can be used in this invention. Apixaban may be obtained directly via the synthesis described in U.S. Pat. No. 6,967,208 and/or US20060069258A1 (based on U.S. application Ser. No. 11/235,510 filed Sep. 26, 2005), herein incorporated by reference.

Form N-1 (neat) and Form H2-2 (hydrate) of apixaban may be characterized by unit cell parameters substantially equal to the following shown in Table 1.

TABLE 1

| Form | N-1 | H2-2 |
|---|---|---|
| Solvate | None | Dihydrate |
| T | +22 | +22 |
| a(Å) | 10.233(1) | 6.193(1) |
| b(Å) | 13.852(1) | 30.523(1) |
| c(Å) | 15.806(1) | 13.046(1) |
| α, ° | 90 | 90 |
| β, ° | 92.98(1) | 90.95(1) |
| γ, ° | 90 | 90 |
| V(Å³) | 2237.4(5) | 2466.0(5) |
| Z' | 1 | 1 |
| Vm | 559 | 617 |
| SG | $P2_1/n$ | $P2_1/n$ |
| Dcalc | 1.364 | 1.335 |
| R | 0.05 | 0.09 |
| Sol. sites | None | 2 $H_2O$ |

Z' is the number of molecules per asymmetric unit.
T(° C.) is the temperature for the crystallographic data.
Vm = V(unit cell)/(ZZ')

Characteristic X-ray diffraction peak positions (degrees 2θ±0.1) at room temperature, based on a high quality pattern collected with a diffractometer (CuKα) with a spinning capillary with 2θ calibrated with a NIST suitable standard are shown in Table 2 below.

TABLE 2

| Form N-1 | Form H2-2 |
|---|---|
| 10.0 | 5.8 |
| 10.6 | 7.4 |
| 12.3 | 16.0 |
| 12.9 | 20.2 |
| 18.5 | 23.5 |
| 27.1 | 25.2 |

It will be appreciated by those skilled in the art of manufacturing and granulation processes that there are numerous known methods which can be applied to producing apixaban solid dosage forms. The feature of this invention, however, involves processes that produce apixaban dosage forms with an ability to produce primary particles at the site of dissolution with a d90<89 μm. Examples of such methods include as well as dry granulation or wet-granulation by low or high-shear techniques The dry granulation process that produces crystalline apixaban particles having a mean particle size equal to or less than about 89 μm, is believed to be novel, and is accordingly provided as a further feature of the invention. Thus, the invention provides a drug product manufacturing process, comprising the steps:

(1) Blend the raw materials required prior to granulation;
(2) Granulate the raw materials from Step 1 using a dry or wet granulation process;
(3) Blend the sized granules from step 3 with extragranular raw materials;
(4) Compress the blend from Step 3 into tablets; and
(5) Film coat the tablets from step 4.

In another embodiment, the invention provides a drug product manufacturing process, comprising the steps:

(1) Blend the raw materials, with apixaban of controlled particle size;
(2) Include intragranular portions of binder, disintegrant and other fillers in the mix from step (1);
(3) Granulate the materials from step (2) using process (3a) or (3b):
  (3a) DRY GRANULATION: Delump the intragranular lubricant using a suitable screen or mill. Add the lubricant to the blend from step (2) and blend. Compact the lubricated blend to ribbons of density in the range of 1.0 to 1.2 g/cc and size the compacted ribbons using a roller compactor; or
  (3b) WET GRANULATION: Wet granulate the composition from step
(2) using water to a target end point and optionally, size the wet-granules by passing through a screen/mill. Remove water for granulation by drying in a convection oven or a fluid-bed dryer. Size the dried granules by passing through a screen/mill;
(4) Blend the sized granules from step (3) and the extragranular disintegrant in a suitable blender;
(5) Delump the extragranular lubricant using a suitable screen/mill and blend with granules from step (4);
(6) Compress the blend from (5) into tablets;
(7) Film coat the tablets from step (6).

In a preferred embodiment, a dry granulation process is employed.

In a preferred embodiment, the surfactant (SLS) in the composition serves as a wetting aid for inherently hydrophobic apixaban drug substance (contact angle=54° with water), further exacerbated as part of air-jet milling process that is used to reduce apixaban particle size to the desired size.

The amount of apixaban contained in a tablet, capsule, or other dosage form containing a composition of this invention will usually be between 2.5 and 5 mg, usually administered orally twice a day, although amounts outside this range and different frequencies of administration are feasible for use in therapy as well. As previously mentioned, such dosage forms are useful, inter alia, in the prevention and/or treatment of thromboembolic disorders, for example, deep vein thrombosis, acute coronary syndrome, stroke, and pulmonary embolism, as disclosed in U.S. Pat. No. 6,967,208.

As noted, average particle size can be determined by Malvern light scattering, a laser light scattering technique. In the examples below, the particle size for apixaban drug substance was measured using a Malvern particle size analyzer.

Upon measurement completion, the sample cell was emptied and cleaned, refilled with suspending medium, and the sampling procedure repeated for a total of three measurements.

The dissolution test is performed in 900 mL of dissolution medium at 37° C., using USP Apparatus 2 (paddles) method at a rotation speed of 75 rpm. Samples are removed after 10, 20, 30, 45, and 60 minutes from test initiation and analyzed for apixaban by HPLC at 280 nm. 0.1 N HCl or 0.05 M sodium phosphate pH 6.8 with 0.05% SDS solution has been used as dissolution medium during formulation development. While both methods serve the purposes as quality control tests (with adequate discrimination ability), and in establishing IVIVR, the latter was preferred from the standpoint of method robustness. A role of SDS (surfactant) in the latter dissolution medium is as a wetting aid to facilitate complete dissolution of hydrophobic apixaban from tablets, rather than to increase the solubility of apixaban. Dissolution data from both the tests are included in this invention record and unless otherwise specified, the results reported were averages of values from six tablets.

Blood samples are drawn at predetermined time points following drug administration as specified in the clinical study protocol. Concentrations of the samples are measured using a validated analytical method (Liquid Chromatography with Tandem Mass Spectrometry). Individual subject pharmacokinetic parameters (eg, Cmax, AUC, T-HALF) are derived by non-compartmental methods using Kinetica® software from the time-concentration profiles.

The invention is further exemplified and disclosed by the following non-limiting examples:

Table 3 shows apixaban tablet compositions prepared using the drygranulation process that were evaluated in bioequivalence (BE) study.

TABLE 3

| | Dry Granulation | |
|---|---|---|
| Ingredients | 5% w/w Drug Loaded Granulation (% w/w) | 20 mg Tablet (mg/tablet) |
| Intragranular | | |
| Apixaban | 5.00 | 20.00 |
| Lactose Anhydrous | 49.25 | 197.00 |
| Microcrystalline Cellulose | 39.50 | 158.00 |

TABLE 3-continued

|  | Dry Granulation | |
|---|---|---|
| Ingredients | 5% w/w Drug Loaded Granulation (% w/w) | 20 mg Tablet (mg/tablet) |
| Croscarmellose Sodium | 2.00 | 8.00 |
| Magnesium Stearate | 0.50 | 2.00 |
| Sodium Lauryl Sulfate | 1.00 | 4.00 |
| Extragranular | | |
| Croscarmellose Sodium | 2.00 | 8.00 |
| Magnesium Stearate | 0.75 | 3.00 |
| Total | 100.00 mg | 400 mg |
| Film Coat | 3.5 | 14.0 |
| Total | 103.5 mg | 414 mg |

Table 4 shows apixaban tablet compositions prepared using the wet granulation process that were evaluated in BE study.

TABLE 4

|  | Wet Granulation | |
|---|---|---|
| Ingredients | 5% w/w Drug Loaded Granulation (% w/w) | 20 mg Tablet (mg/tablet) |
| Intragranular | | |
| Apixaban | 5.00 | 20.00 |
| Lactose Monohydrate | 70.00 | 280.00 |
| Microcrystalline Cellulose | 5.00 | 60.00 |
| Croscarmellose Sodium | 2.50 | 10.00 |
| Povidone | 4.50 | 18.00 |
| Purified Water | 17.40 | 69.60 |
| Extragranular | | |
| Croscarmellose Sodium | 2.50 | 10.00 |
| Magnesium Stearate | 0.50 | 2.09 |
| Microcrystalline Cellulose | 10.00 | 10.09 |
| Total | 100.00 | 400.00 |
| Film Coat | 3.5 | 14.0 |
| Total | 103.5 mg | 414.0 |

Table 5 and Table 5a show the dissolution data that indicates that having a dry granulation process will result in faster dissolution compared to that from a wet granulation process. As shown in Table 5, the 20 mg tablets made using a dry granulation process had 79% apixaban dissolved in 30 minutes versus 62% apixaban dissolved at 30 minutes for the 20 mg tablets made using a wet granulation process. Dissolution test in 0.1N HCl also indicated a similar behavior of faster dissolution from tablets made using dry granulation process (58% in 30 min), compared to wet granulation process (45% in 30 min).

TABLE 5

|  | % apixaban dissolved (USP II, 75 rpm, 0.05% SLS in 50 mM phosphate, pH 6.8) | |
|---|---|---|
| Time (minutes) | Wet Granulation 20 mg Tablets | Dry Granulation 20 mg Tablets |
| 10 | 38 | 47 |
| 20 | 54 | 70 |
| 30 | 62 | 79 |
| 45 | 71 | 86 |
| 60 | 76 | 90 |
| API Particle Size $D_{90}$ (μm) | 83.8 | 83.8 |

TABLE 5a

|  | % apixaban dissolved (USP II, 75 rpm, 0.1N HCl) | |
|---|---|---|
| Time (minutes) | Wet Granulation 20 mg Tablets | Dry Granulation 20 mg Tablets |
| 10 | 30 | 41 |
| 20 | 39 | 52 |
| 30 | 45 | 58 |
| 45 | 51 | 64 |
| 60 | 56 | 68 |
| 90 | 64 | 74 |
| API Particle Size $D_{90}$ (μm) | 83.8 | 83.8 |

Table 6 and Table 6a provides the dissolution data from tablets made with different manufacturing pprocesses (wet and dry granulation) and drug substance different particle sizes. As shown Table 6, apixaban tablets that had 77% dissolved in 30 minutes or 86% dissolved in 30 minutes both had AUC values that met bioequivalence criteria (Confidence Interval between 80% to 125%) when compared to the tablets that had 89% dissolved at 30 minutes. Similar rank order of the dissolution rates were observed for these tablets (A, B & C) when tested in 0.1N HCl.

TABLE 6

|  | % apixaban dissolved (USP II, 75 rpm, 0.05% SLS in 50 mM phosphate, pH 6.8) | | |
|---|---|---|---|
| Time (minutes) | Wet Granulation 2 × 2.5 mg Tablets (A) | Wet Granulation 2 × 2.5 mg Tablets (B) | Dry Granulation 2 × 2.5 mg Tablets (C) |
| 10 | 63 | 42 | 70 |
| 20 | 79 | 64 | 84 |
| 30 | 86 | 77 | 89 |
| 45 | 91 | 87 | 94 |
| 60 | 94 | 93 | 96 |
| $C_{max}$ (ng/mL) | 101.8 (21) | 87.8 (24) | 108.3 (24) |
| AUC(INF) (ng*hr/mL) | 1088 (32) | 1030 (25) | 1153 (26) |

Geomean (CV %) are presented for Cmax and AUC(INF)

TABLE 6a

|  | % apixaban dissolved (USP II, 75 rpm, 0.1N HCl) | | |
|---|---|---|---|
| Time (minutes) | Wet Granulation 2 × 2.5 mg Tablets (A) | Wet Granulation 2 × 2.5 mg Tablets (B) | Dry Granulation 2 × 2.5 mg Tablets (C) |
| 10 | 44 | 25 | 56 |
| 20 | 62 | 43 | 71 |
| 30 | 72 | 54 | 79 |

TABLE 6a-continued

| | % apixaban dissolved (USP II, 75 rpm, 0.1N HCl) | | |
|---|---|---|---|
| Time (minutes) | Wet Granulation 2 × 2.5 mg Tablets (A) | Wet Granulation 2 × 2.5 mg Tablets (B) | Dry Granulation 2 × 2.5 mg Tablets (C) |
| 45 | 80 | 66 | 85 |
| 60 | 84 | 74 | 88 |
| AUC(INF) (ng*hr/mL) | 1088 (32) | 1030 (25) | 1153 (26) |

Geomean (CV %) are presented for Cmax and AUC(INF)

The results of clinical studies demonstrated that, for tablets with similar dissolution rates (89% and 86% at 30 min in pH 6.8 phosphate buffer containing 0.05% SLS), Cmax and AUC of the coated Phase 3 tablet (C) relative to the uncoated Phase 2 tablet (A), met bioequivalence criteria. Tablets with different dissolution rates (77% and 86% at 30 min) had similar AUCs, but did not meet equivalence criteria for Cmax. The lower boundary of the 90% confidence interval of ratio of geometric mean Cmax was 0.788, indicating the rate of absorption, as defined by Cmax, was lower for the slower dissolving tablet (77% at 30 min). Since the oral bioavailability from these tablets is shown to be comparable to that from solution (see FIGS. 1 and 2 below), this dissolution rate (77% in 30 min) is defined as the threshold for achieving consistent exposure.

FIGS. 3 and 4 illustrate the dissolution data that shows that while particle size impacts dissolution, controlling the particle size to less than 89 microns will result in a dissolution rate that will ensure consistent in-vivo exposures. As indicated in FIGS. 3 and 4, consistent exposures are expected once apixaban tablets have greater than 77% apixaban dissolved in 30 minutes. Since the tablets with 89 microns have >77% dissolved at 30 minutes, these tablets will also exhibit exposures that are equivalent to the exposures from tablets made with smaller particles (such as the tablets with 10 micron particles shown below). Whilst dissolution rate at an apixaban particle size of 119 microns is marginally greater than 77% in 30-min for the 5-mg apixaban tablets (FIG. 4), the particle size threshold claimed is less than 89 microns. This allows for the typical variability (RSD=2 to 3%) in the dissolution results, such that the oral bioavailability from tablets consistently matches that from solution.

What is claimed is:

1. A solid pharmaceutical composition comprising a therapeutically effective amount of crystalline apixaban particles and a pharmaceutically acceptable diluent or carrier,
   wherein the crystalline apixaban particles have a $D_{90}$ equal to or less than about 89 μm, and
   wherein at least 77 wt % of apixaban dissolves within 30 minutes in a pH 6.8 phosphate buffer containing 0.05% sodium lauryl sulfate.

2. The composition as defined in claim 1, wherein said composition comprises Form N-1 of apixaban.

3. The composition as defined in claim 1, wherein the $D_{90}$ is equal to or less than 85 μm.

4. The composition as defined in claim 1, wherein the $D_{90}$ is equal to or less than 50 μm.

5. The composition as defined in claim 1, wherein the $D_{90}$ is equal to or less than 30 μm.

6. The composition as defined in claim 1, wherein the $D_{90}$ is equal to or less than 25 μm.

7. The composition as defined in claim 1, further comprising:
   from 1% to 2% by weight of a surfactant.

8. The composition as defined in claim 7, wherein the surfactant is sodium lauryl sulfate.

9. The composition as defined in claim 1, wherein the pharmaceutical composition comprises from about 2.5 mg to about 5 mg of apixaban.

10. The composition as defined in claim 1, wherein the pharmaceutical composition comprises 2.5 mg of apixaban.

11. The composition as defined in claim 1, wherein the pharmaceutical composition comprises 5 mg of apixaban.

12. A solid pharmaceutical composition comprising a therapeutically effective amount of apixaban and a pharmaceutically acceptable diluent or carrier,
   wherein apixaban comprises crystalline apixaban particles,
   wherein the crystalline apixaban particles have a $D_{90}$ equal to or less than about 89 μm, and
   wherein, as measured using a USP Apparatus 2 at a paddle rotation speed of 75 rpm in 900 mL, of a dissolution medium at 37° C., at least 77 wt % of apixaban in the pharmaceutical composition dissolves within 30 minutes in the dissolution medium, and the dissolution medium is 0.05 M sodium phosphate at a pH 6.8 containing 0.05% sodium lauryl sulfate.

13. The composition as defined in claim 12, wherein said composition comprises Form N-1 of apixaban.

14. The composition as defined in claim 12, wherein the $D_{90}$ is equal to or less than 85 μm.

15. The composition as defined in claim 12, wherein the $D_{90}$ is equal to or less than 50 μm.

16. The composition as defined in claim 12, wherein the $D_{90}$ is equal to or less than 30 μm.

17. The composition as defined in claim 12, wherein the $D_{90}$ is equal to or less than 25 μm.

18. The composition as defined in claim 12, further comprising:
   from 1% to 2% by weight of a surfactant.

19. The composition as defined in claim 18, wherein the surfactant is sodium lauryl sulfate.

20. The composition as defined in claim 12, wherein the pharmaceutical composition comprises from about 2.5 mg to about 5 mg of apixaban.

21. The composition as defined in claim 12, wherein the pharmaceutical composition comprises 2.5 mg of apixaban.

22. The composition as defined in claim 12, wherein the pharmaceutical composition comprises 5 mg of apixaban.

23. The composition as defined in claim 1, which is a tablet.

24. The composition as defined in claim 1, which is a capsule.

25. The composition as defined in claim 9, which is a tablet.

26. The composition as defined in claim 9, which is a capsule.

27. The composition as defined in claim 10, which is a tablet.

28. The composition as defined in claim 10, which is a capsule.

29. The composition as defined in claim 11, which is a tablet.

30. The composition as defined in claim 11, which is a capsule.

31. The composition as defined in claim 12, which is a tablet.

32. The composition as defined in claim 12, which is a capsule.

33. The composition as defined in claim 20, which is a tablet.

34. The composition as defined in claim 20, which is a capsule.

35. The composition as defined in claim 21, which is a tablet.

36. The composition as defined in claim 21, which is a capsule.

37. The composition as defined in claim 22, which is a tablet.

38. The composition as defined in claim 22, which is a capsule.

* * * * *